United States Patent [19]

Klein et al.

[11] 3,968,173

[45] July 6, 1976

[54] PROCESS FOR THE PREPARATION OF 5-ISOPROPYL-3-METHYL-PHENOL

[75] Inventors: Alfons Klein, Duesseldorf; Karlfried Wedemeyer, Cologne, both of Germany

[73] Assignee: Bayer Aktiengesellschaft, Leverkusen, Germany

[22] Filed: Aug. 22, 1973

[21] Appl. No.: 390,449

[30] Foreign Application Priority Data

Aug. 30, 1972 Germany............................ 2242628

[52] U.S. Cl............................ 260/626 T; 260/624 E
[51] Int. Cl.².......................................... C07C 39/06
[58] Field of Search............ 260/624, 624 E, 626 R, 626 T

[56] References Cited
FOREIGN PATENTS OR APPLICATIONS

| | | | |
|---|---|---|---|
| 2,027,610 | 12/1971 | Germany | 260/624 |
| 2,039,600 | 1/1971 | Germany | 260/624 |
| 2,101,014 | 10/1971 | Germany | 260/624 |

OTHER PUBLICATIONS

Pigman et al., "J. Amer. Chem. Soc.," vol. 76, (1954), pp. 6169–6171.

Primary Examiner—James O. Thomas, Jr.
Assistant Examiner—W. B. Lone
Attorney, Agent, or Firm—Burgess, Dinklage & Sprung

[57] ABSTRACT

In the preparation of 5-isopropyl-3-methyl-phenol from 3-methyl-phenol carrying at least one isopropyl radical or in the presence of propene by heating in the presence of a catalyst, the improvement which comprises effecting said heating at a temperature of about 200° to 400°C in the presence, as a catalyst, of synthetic aluminum silicate which has not been treated with acid. The reaction can involve isopropylation, isomerization and/or transisopropylation.

8 Claims, No Drawings

PROCESS FOR THE PREPARATION OF 5-ISOPROPYL-3-METHYL-PHENOL

The present invention relates to an unobvious process for the preparation of 5-isopropyl-3-methyl-phenol, which can be used as an intermediate in the synthesis of insecticides.

It has been disclosed in German Published Specification DOS No. 2,101,014 that 5-isopropyl-3-methyl-phenol can be prepared by isomerization of 6-isopropyl-3-methyl- phenol in 1,2-dichloroethane with anhydrous aluminum chloride. For this, 1 to 2 moles of aluminum chloride are required per mole of starting material.

The use of aluminum chloride requires working under anhydrous conditions, which necessitates additional drying of the starting phenols, which are in most cases moist, and furthermore adds significantly to the expense of the solvents to be employed.

It has also been disclosed in German Published Specification DOS No. 2,039,600 that 5-isopropyl-3-methyl-phenol can be prepared by the reaction of 3-methyl-phenol with propene in the presence of an aqueous solution of zinc bromide or zinc chloride, with addition of hydrogen bromide or hydrogen chloride. In both cases, strongly acid catalysts are used, which leads to considerable corrosion problems if the process is employed industrially.

The present invention provides an improvement in the process for the preparation of 5-isopropyl-3-methyl-phenol from 3-methyl-phenol carrying at least one isopropyl radical or in the presence of propene by heating in the presence of a catalyst. Specifically, the improvement comprises effecting said heating at a temperature of about 200° to 400°C in the presence, as a catalyst, of synthetic aluminum silicate which has not been treated with acid. Thus the reaction involves alkylation of 3-methyl-phenol with propene, and/or the rearrangement of one or more isomeric monoisopropyl-3-methyl-phenols, and/or the transalkylation of one or more polyisopropyl-3-methyl-phenols and 3-methyl-phenol. The process may be effected, if appropriate, in the presence of a diluent or solvent.

The present invention is capable of producing 5-isopropyl-3-methyl-phenol in a simple and economical manner, even on an industrial scale.

The use of such synthetic aluminum silicates that have not been treated with acid has been disclosed for the isomerization of monoalkylphenols such as ethylphenols or isopropylphenols. For example, in German Published Specification DOS No. 2,027,610 a mixture of 1.5% of 3-isopropyl-phenol,
20.5% of 4-isopropyl-phenol,
58.8% of 2-isopropyl-phenol and
23.2% of diisopropylphenols is isomerized in the presence of syntheitc aluminum silicate at 320°C. It yields the following thermodynamic equilibrium:

41.5% of 3-isopropyl-phenol,
19.7% of 4-isopropyl-phenol, 18.5% of 2-isopropyl-phenol and
18.5% of 2-isopropyl-phenol and
20.3% of diisopropylphenols.

The proportion of diisopropylphenols remains practically unchanged. Of the three possible monoisopropylphenols, the 3-isomer predominates. Further by-products are not to be expected.

It should be noted that the compound to be prepared according to the invention is a dialkylphenol.

According to the present invention, monoisopropyl-3-methyl-phenols, that is to say dialkylphenols, are subjected to isomerization with aluminum silicates which have not been treated with acid. In such an isomerization, 10 isomers would be possible if both alkyl groups migrate (J. Am. Chem. Soc. 76, page 6169).

It is also known that dialkylphenols tend to disproportionate to give trialkylphenols and monoalkylphenols. Further by-products would be expected due to such a reaction.

Though, in general, methyl groups in phenols tend to isomerize less easily than isopropyl groups, the literature shows (J. Am. Chem. Soc. 76, page 6169) that 3-methyl-phenol, for example, isomerizes or disproportionates in the presence of an aluminum silicate, at 344°C, to give the following mixture:

| | | |
|---|---|---|
| Phenol | = | 17.3% |
| Isomeric methylphenols | = | 35.2% |
| Dimethylphenols | = | 17.2% |
| Neutral substances | = | 2.5% |
| Residue | = | 21.4% |
| Carbon | = | 6.4%. |

It is therefore surprising that in the process according to the invention 5-isopropyl-3-methyl-phenol is produced in good yields because, in view of the state of the art, it had to be expected that a large number of isomers would be produced through migration of the methyl group.

As compared to the prior-art processes for the preparation of 5-isopropyl-3-methyl-phenol, the process according to the invention shows various advantages. Thus, no corrosion problems arise because no strongly acid materials are used. Furthermore, the removal of the catalyst is simpler. After completion of the reaction, the reaction mixture is freed of the contact catalyst by filtration.

The aluminum silicate catalysts which are suitable for use in the process according to the invention are, in general, the known silicon dioxide-aluminum oxide catalysts used in cracking hydrocarbons. They generally comprise about 1 –50 percent by weight of aluminum oxide and 99 –50 percent by weight of silicon dioxide, and preferably about 1 –20 percent of aluminum oxide and 99 –80 percent of silicon dioxide. LeA 14622 They have not been treated with acids.

If 5-isopropyl-3-methyl-phenol is to be prepared according to the invention by reaction of 3-methyl-phenol with propene, this reaction is carried out at temperatures of about 200° to 400°C, preferably about 250° to 350°C.

It is however also possible first to carry out the alkylation at temperatures of about 100° to 200°C, preferably between 130° and 170°C. This produces an isomer mixture which consists predominantly of 6-isopropyl-3-methyl-phenol. Thereafter, the isomerization is carried out at temperatures of about 200° to 400°C, preferably between 250° and 350°C. As noted, the reactions can be effected stepwise or concurrently.

In the reaction, the molar ratio of 3-methyl-phenol to propene can be varied over a wide range. Thus it is possible to employ 3-methyl-phenol and propene in an approximately equimolar ratio. On the other hand, however, an excess of 3-methyl-phenol is preferably used since in that case particularly high yields are achieved.

The reaction can be carried out under normal pressure or elevated pressure.

Appropriately, about 2 to 20 percent by weight of catalyst, preferably 7 to 14 percent by weight, are used relative to 3-methyl-phenol employed.

A further variant of the process according to the invention is the direct isomerization of monoisopropyl-3-methyl-phenols.

Either the individual isomeric monoisopropyl-3-methyl-phenols in the pure form, or their mixtures, can be used as the starting material for this isomerization.

To avoid side-reactions it is desirable to add 3-methyl-phenol to the starting material.

This added amount can be about 0.1 to 5 moles of 3-methyl-phenol per mole of monoisopropyl-3-methyl-phenol employed, preferably between 0.5 and 2 moles of 3-methyl-phenol per mole of monoisopropyl-3-methyl-phenol.

The isomerization is carried out at temperatures of about 200° to 400°C, preferably between 250° and 350°C. It can be carried out under normal pressure or elevated pressure.

Appropriately, about 2 to 20 percent by weight of catalyst, preferably 7 to 14 percent by weight, are used relative to the total amount of alkylated phenol employed.

To prepare 5-isopropyl-3-methyl-phenol according to the invention it is also possible to start from more highly propylated 3-methyl-phenol. Thus, for example, di-, tri-, or tetra-isopropyl-3-methyl-phenols can be used.

These polyisopropyl-3-methyl-phenols can be employed individually or as mixtures.

Appropriately, the procedure followed is to add 3-methyl-phenol to the more highly propylated 3-methyl-phenols and to expose this mixture to the conditions according to the invention. Hereupon, 5-isopropyl-3-methyl-phenol is formed by trans-alkylation.

The amount of the added 3-methyl-phenol depends on the amount and nature of polypropyl-3-methyl-phenol employed.

In this trans-alkylation, the molar ratio between each isopropyl group to be transferred and 3-methyl-phenol can be varied over a wide range. Thus it is possible to employ an equimolar amount of 3-methyl-phenol for each isopropyl group to be transferred. Preferably, however, an excess of 3-methyl-phenol is used, leading to particularly high yields.

The trans-alkylation is carried out at temperatures of about 200° to 400°C, preferably between 250° and 350°C. It can be carried out under normal pressure or elevated pressure.

Appropriately, about 2 to 20 percent by weight of catalyst, preferably 7 to 14 percent by weight, are used based on the total amount of alkyl phenol employed.

The methods of alkylation, isomerization and trans-alkylation which have been mentioned and which lead, according to the invention, to 5-isopropyl-3-methyl-phenol, can also be combined with one another.

Thus it is possible, for example, to subject mixtures of 3-methyl-phenol, monoisopropyl-3-methyl-phenols and polyisopropyl-3-methyl-phenols to the conditions according to the invention. Hereupon, isomerization and trans-alkylation reactions take place simultaneously.

In a similar manner, the alkylation, if initially carried out at low temperatures, can lead to mixtures of mono- and poly-isopropyl-3-methyl-phenols. After addition of 3-methyl-phenol, these mixtures are subjected to the conditions according to the invention. They lead, in good yields, to 5-isopropyl-3-methyl-phenol.

The listed methods of alkylation, isomerization and trans-alkylation, which lead, according to the invention, to 5-isopropyl-3-methyl-phenol, can be carried out in the presence of inert diluents, if appropriate. For this purpose, aliphatic hydrocarbons such as hexane and heptane, and aromatic hydrocarbons such as benzene, toluene and xylene, are particularly suitable.

The reaction product can be worked up in the usual manner by removing the catalyst by filtration and isolating 5-isopropyl-3-methyl-phenol from the filtrate by distillation or crystallization.

The process can also be carried out continuously if, in a suitable apparatus, either propene is allowed to act on 3-methyl-phenol or other starting materials according to the invention are treated in the presence of the synthetic aluminum silicate which has not been treated with acid.

5-Isopropyl-3-methyl-phenol, obtainable according to the invention, can be used as an intermediate for the preparation of the known insecticide 3-methyl-5-isopropyl-phenylmethyl carbamate as described in German Published Specification DAS No. 1,156,272.

The invention is illustrated in the following preparative Examples.

EXAMPLE 1

63 g (1.5 moles) of propene were pumped, over the course of one hour, into 324 g (3 moles) of 3-methyl-phenol and 40 g of a synthetic aluminum silicate, containing about 85 percent of silicon dioxide, in an autoclave at 150°C. Thereafter the mixture was stirred for 6 hours at 300°C. After removing the catalyst by filtration and separating off 177 g of excess 3-methyl-phenol by distillation, 195 g of an alkylation product having the followng composition were obtained:

| | | |
|---|---|---|
| 6-Isopropyl-3-methyl-phenol | = | 20.3% |
| 5-Isopropyl-3-methyl-phenol | = | 64.3% |
| 4-Isopropyl-3-methyl-phenol | = | 6.3% |
| Diisopropyl-3-methyl-phenols | = | 5.3% |
| Other alkylated phenols | = | 4.1% |

EXAMPLE 2

A mixture of 150 g of 6-isopropyl-3-methyl-phenol and 100 g of 3-methyl-phenol was stirred for 4 hours at 300°C in the presence of 20 g of a synthetic aluminum silicate containing about 86 percent of silicon dioxide. After removing the catalyst and separating off 105 g of 3-methyl-phenol by distillation, 125 g of an alkylation product having the following composition were obtained:

| | | |
|---|---|---|
| 6-Isopropyl-3-methyl-phenol | = | 15.3% |
| 5-Isopropyl-3-methyl-phenol | = | 65.0% |
| 4-Isopropyl-3-methyl-phenol | = | 4.7% |
| Diisopropyl-3-methyl-phenols | = | 6.1% |
| Other alkylated phenols | = | 8.9% |

EXAMPLE 3

47.7 g of 4,6-diisopropyl-3-methyl-phenol, 75 g of 3-methyl-phenol and 10 g of a synthetic aluminum silicate containing about 86 percent of silicon dioxide were stirred for 5 hours at 300°C in an autoclave. After removing the catalyst and separating off 54 g of 3-methyl-phenol by distillation, 66 g of an alkylation product of the following composition were obtained:

| | | |
|---|---|---|
| 6-Isopropyl-3-methyl-phenol | = | 16.2% |
| 5-Isopropyl-3-methyl-phenol | = | 60.3% |
| 4-Isopropyl-3-methyl-phenol | = | 4.5% |
| Diisopropyl-3-methyl-phenols | = | 9.2% |
| Other alkylated phenols | = | 9.7%. |

EXAMPLE 4

A mixture of the following composition:

| | | |
|---|---|---|
| 3-Methyl-phenol | = | 29.6% |
| 6-Isopropyl-3-methyl-phenol | = | 49.8% |
| 5-Isopropyl-3-methyl-phenol | = | 2.0% |
| 4-Isopropyl-3-methyl-phenol | = | 1.7% |
| Diisopropyl-3-methyl-phenols | = | 16.4% |
| Other alkylated phenols | = | 0.5% | was stirred for 6 hours at 300°C in an autoclave with 8 percent of a synthetic aluminum silicate containing about 86 percent of silicon dioxide. The reaction product obtained after removal of the catalyst had the following composition:

| | | |
|---|---|---|
| 3-Methyl-phenol | = | 35.5% |
| 6-Isopropyl-3-methyl-phenol | = | 11.7% |
| 5-Isopropyl-3-methyl-phenol | = | 40.5% |
| 4-Isopropyl-3-methyl-phenol | = | 2.5% |
| Diisopropyl-3-methyl-phenols | = | 6.3% |
| Other alkylated phenols | = | 3.5%. |

It will be appreciated that the instant specification and examples are set forth by way of illustration and not limitation, and that various modifications and changes may be made without departing from the spirit and scope of the present invention.

What is claimed is:

1. In a process for the preparation of 5-isopropyl-3-methyl phenol comprising heating a material low in 5-isopropyl-3-methyl phenol and containing at least one of diisopropyl-3-methyl phenol and o- or p-isopropyl-3-methyl phenol at a temperature between 200°C and 400°C the improvement which comprises effecting the heating in an autoclave in the presence of synthetic aluminum silicate that has not been treated with acid as a catalyst, the catalyst being present in about 2 to 20 percent by weight of the starting methyl phenols, whereby there is produced a mixture predominantly comprising 5-isopropyl-3-methyl-phenol and low in diisopropyl-3-methyl phenols.

2. A process according to claim 1 where the material relatively low in 5-isopropyl-3-methyl phenol is produced by reaction of 3-methyl phenol with propene.

3. A process according to claim 1 wherein the material relatively low in 5-isopropyl-3-methyl phenol is an isomeric mono isopropyl-3-methyl phenol.

4. A process according to claim 1 wherein the material relatively low in 5-isopropyl-3-methyl phenol comprises a polyisopropyl-3-methyl phenol and 3-methyl phenol which are trans-alkylated.

5. The process according to claim 1 wherein heating is effected in the presence of about 0.1 to 5 moles of 3-methyl-phenol per mole of monoisopropyl-3-methyl-phenol other than the 5-isopropyl-isomer.

6. The process according to claim 1, wherein heating is effected in the presence of an inert hydrocarbon as diluent.

7. The process according to claim 1, wherein the aluminum silicate comprises about 1 to 50 percent by weight of aluminum oxide and 99 to 50 percent by weight of silicon dioxide.

8. The process according to claim 1, wherein the aluminum silicate is used in about 7 to 14 percent by weight of the alkyl-phenol and comprises about 1 to 20 percent by weight of aluminum oxide and 99 to 80 percent by weight of silicon dioxide, heating being effected at about 250° to 350°C.

* * * * *